US008906659B2

(12) United States Patent
Clyne et al.

(10) Patent No.: US 8,906,659 B2
(45) Date of Patent: Dec. 9, 2014

(54) PLASMA TREATMENT FOR GROWTH FACTOR RELEASE FROM CELLS AND TISSUES

(75) Inventors: Alisa Morss Clyne, Ardmore, PA (US); Gennady Friedman, Richboro, PA (US); Alexander Fridman, Philadelphia, PA (US); Sameer Kalghatgi, Waltham, MA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 13/256,558

(22) PCT Filed: Mar. 16, 2010

(86) PCT No.: PCT/US2010/027411
§ 371 (c)(1),
(2), (4) Date: Dec. 6, 2011

(87) PCT Pub. No.: WO2010/107745
PCT Pub. Date: Sep. 23, 2010

(65) Prior Publication Data
US 2012/0135390 A1    May 31, 2012

Related U.S. Application Data

(60) Provisional application No. 61/160,496, filed on Mar. 16, 2009.

(51) Int. Cl.
*C12N 13/00* (2006.01)
*A01N 1/02* (2006.01)
*C12N 5/071* (2010.01)
*A01N 1/00* (2006.01)
*A61N 5/10* (2006.01)

(52) U.S. Cl.
CPC ............ *C12N 5/069* (2013.01); *C12N 2500/02* (2013.01)
USPC ........................ 435/173.8; 435/1.1; 435/173.1

(58) Field of Classification Search
None
See application file for complete search history.

(56) References Cited

U.S. PATENT DOCUMENTS 7,691,101 B2 *  4/2010  Davison et al. ................. 606/41
2007/0213700 A1   9/2007  Davison et al.

OTHER PUBLICATIONS

Kieft, I.E.; et al; "Non-thermal plasma treatment of ex vivo arteries: preliminary results" XXVIIth ICPIG, Eindhoven, the Netherlands, Jul. 18-22, 2005.*
Stoffels, Eva; et al; "Delayed Effects of Cold Atmospheric Plasma on Vascular Cells" Plasma Processes and Polymers, 5, 599-605, 2008.*
Fridman, Gregory; et al; "Bio-medical applications of non-thermal atmospheric pressure plasma" 37th AIAA Plasmadynamics and Lasers Conference. 2006.*
Bailey, Steve R.; et al; "Angiogenic bFGF expression from gas-plasma treated scaffolds" Cardiovascular Radiation Medicine, 3, 183-189, 2002.*
Callaghan et al., "Pulsed Electromagnetic Fields Accelerate Normal and Diabetic Wound Healing by Increasing Endogenous FGF-2 Release", Plastic and Reconstructive Surgery, Jan. 2008, 121(1), 130-141.
Fridman et al., "Comparison of Direct and Indirect Effects of Non-Thermal Atmospheric-Pressure Plasma on Bacteria", Plasma Processes and Polymers, Communication, May 23, 2007, 4, 370-375.
Kalghatgi et al., "Non-Thermal Dielectric Barrier Discharge Plasma Teatment of Endothelial Cells", 30th Annual International Conference of the IEEE in Medicine and Biology Society, EMBS 2008, Aug. 20-25, 2008, 3578-3581.
PCT Application No. PCT/US2010/027411 : International Preliminary Report on Patentability, Sep. 20, 2011, 6 pages.
PCT Application No. PCT/US2010/027411 : International Search Report and Written Opinion of the International Searching Authority, May 26, 2010, 8 pages.

* cited by examiner

*Primary Examiner* — Blaine Lankford
*Assistant Examiner* — David Berke-Schlessel
(74) *Attorney, Agent, or Firm* — Baker & Hostetler LLP

(57) ABSTRACT

Aspects of the present invention are related to methods comprising contacting an endothelial cell in an endothelial cell population with a non-thermal plasma to release an angiogenic growth factor. The released angiogenic growth factor may induce endothelial cell proliferation. In certain embodiments, the angiogenic growth factor is fibroblast growth factor-2. Preferably, the non-thermal plasma may be an atmospheric pressure dielectric barrier discharge. Additional aspects of the present invention are directed to methods for treating a disease comprising promoting angiogenesis by contacting an endothelial cell in a endothelial cell population with a non-thermal plasma to release an angiogenic growth factor. The angiogenic growth factor may induce endothelial cell proliferation. Further aspects of the present invention are directed to methods for treating a disease comprising inhibiting angiogenesis by contacting an endothelial cell in a endothelial cell population with a non-thermal plasma to reduce the number of endothelial cells in the population.

29 Claims, 15 Drawing Sheets

| Parameter | Value |
|---|---|
| Excitation | Microsecond Pulse |
| Voltage | 20 kV p-p |
| Rise Time | 5 V/ns |
| Pulse Width (FWHM) | 1.65 $\mu$s |
| Frequency | 0.5 - 1.5 kHz |
| Power Density | 0.1 - 1 W / cm$^2$ |
| Rotational Temperature | 300 - 350 K |
| Vibrational Temperature | 3000 - 4000 K |

FIG. 1C

PLASMA TREATMENT FOR GROWTH FACTOR RELEASE FROM CELLS AND TISSUES

CROSS-REFERENCE TO RELATED APPLICATIONS

This application is the National Stage of International Application No. PCT/US2010/027411 filed Mar. 16, 2010, which claims the benefit of U.S. Provisional Application No. 61/160,496, filed Mar. 16, 2009, the disclosures of which are incorporated herein by reference in their entirety.

TECHNICAL FIELD

Aspects of the disclosed invention are in the field of treating endothelial cells for controlling proliferation or apoptosis of endothelial cells. Other aspects of the disclosed invention are in the field of the generation and use of non-thermal plasmas.

BACKGROUND

Endothelial cells, which line all blood contacting surfaces in the body, control many aspects of the vasculature ranging from vascular tone to coagulation to inflammation. Endothelial cells also play a guiding role in angiogenesis, the growth of new blood vessels from existing vessels. Endothelial cells produce and secrete angiogenic growth factors such as fibroblast growth factor-2 (FGF2), which in conjunction with many other signals induce endothelial cells to invade the surrounding tissue, proliferate, and develop into new blood vessels. Angiogenesis can be both helpful and harmful. In wound healing, angiogenesis is required in the wound site for rapid healing, whereas in cancer, angiogenesis blockade can starve a tumor and prevent its growth.

Recently, various treatment techniques have been explored to accelerate angiogenesis and endothelial cell proliferation. One such technique is the addition of exogenous angiogenic growth factors, such as FGF2 or vascular endothelial cell growth factor (VEGF). However, these techniques have had limited success due to challenges in creating the optimal dose, dose gradient, and timing. Exogenous growth factors are also expensive. Other techniques have been shown to release endogenous angiogenic growth factors from cells. These techniques include low dose laser, inductively coupled pulsed electromagnetic fields, pulsed electromagnetic fields (PEMF), and low dose ionizing radiation (LDIR). Although these techniques are useful for endothelial cell proliferation, they are not desirable because they result in damage to surrounding tissue and cells and/or they need extensive and expensive setup to be generated safely and applied to human tissue. Accordingly, a technique useful for endothelial cell proliferation which does not damage tissue and can be controlled to treat specific areas and specific depths of real tissue would be highly desirable.

SUMMARY

Aspects of the present invention are related to methods comprising contacting an endothelial cell population with a non-thermal plasma to release an angiogenic growth factor. The released angiogenic growth factor may induce endothelial cell proliferation. In certain embodiments, the angiogenic growth factor is fibroblast growth factor-2.

The non-thermal plasma may be an atmospheric pressure dielectric barrier discharge plasma. The endothelial cells may be contacted with the non-thermal plasma directly, indirectly, or separately.

The extent of cell proliferation may vary. In certain embodiments, the endothelial cell proliferation results in an increase in the cell population by at least 50%. In other embodiments, the endothelial cell proliferation results in an increase in the cell population by at least 100%. In yet other embodiments, the endothelial cell proliferation results in an increase in the cell population by at least 200%.

The endothelial cells may be contacted with the non-thermal plasma for various amounts of time. In certain embodiments, the endothelial cell is contacted with the non-thermal plasma for less than about 30 seconds. In other embodiments, the endothelia cell is contacted with the non-thermal plasma for less than about 15 seconds. Furthermore, the non-thermal plasma may have an intensity in the range of from about 0.5 J/cm$^2$ to about 6 J/cm$^2$.

Aspects of the present invention are directed to methods wherein the endothelial cell is contacted with a reactive oxygen species produced by the non-thermal plasma. In certain embodiments, the reactive oxygen species are long-living, short-living, or a combination thereof. Long-living reactive oxygen species may include $O_3$, NO, $HO_2$, $H_2O_2$, or a combination thereof. Short-living reactive oxygen species may include OH, O, electrically excited O, $O_2$, or a combination thereof. In certain embodiments, the cell population may be ex vivo tissue, such as, for example, an organ.

Additional aspects of the present invention are directed towards methods for treating a disease by promoting angiogenesis. Angiogenesis may be promoted by contacting an endothelial cell in a endothelial cell population with a non-thermal plasma to release an angiogenic growth factor. The angiogenic growth factor may induce endothelial cell proliferation. In certain embodiments, the disease is diabetic ulcerative wounds. The angiogenic growth factor may be fibroblast growth factor-2 and the non-thermal plasma may be an atmospheric pressure dielectric barrier discharge. The endothelial cells may be contacted with the non-thermal plasma directly, indirectly, or separately.

The endothelial cell proliferation results in an increase in the cell population by at least about 50%, at least about 100%, or at least about 200%. In certain embodiments, the endothelial cell is contacted with the non-thermal plasma for about 30 seconds or less, or about 15 seconds or less. The non-thermal plasma may have an intensity in the range of from about 2 J/cm$^2$ to about 6 J/cm$^2$.

Additional aspects of the present invention are directed to methods for treating a disease comprising inhibition of angiogenesis. Angiogenesis may be inhibited by contacting an endothelial cell in an endothelial cell population with a non-thermal plasma to reduce the number of endothelial cells in the population. The inhibition of angiogenesis is thought to be useful in treating diseases such as cancer. The non-thermal plasma may be atmospheric pressure dielectric barrier discharge. The endothelial cells may be contacted with the non-thermal plasma directly, indirectly, or separately. In some embodiments, the endothelial cell may be contacted with the non-thermal plasma in the range of from about 30 seconds to about 60 seconds, in the range of from about 60 seconds to about 120 seconds, or greater than about 120 seconds. The intensity of the non-thermal plasma may be in the range of from about 6 J/cm$^2$ to about 10 J/cm$^2$.

Further aspects of the present invention are directed to methods comprising contacting endothelial cells in an endothelial cell population with a non-thermal plasma to control the proliferation or apoptosis of the endothelial cells. In certain embodiments, the non-thermal plasma is an atmospheric pressure dielectric barrier discharge. The endothelial cells may be contacted with the non-thermal plasma either directly, indirectly, or separately. In some embodiments, cell proliferation results. The cell population may increase by at least 50%, by at least 100%, or by at least 200%.

The endothelial cells may be contacted with the non-thermal plasma for various amounts of time. For example, in some embodiments, the endothelial cells are contacted with the non-thermal plasma for about 30 seconds or less, or for about 15 seconds or less. In other embodiments, the endothelial cells are contacted with the non-thermal plasma for a time period in the range of from about 30 seconds to about 60 seconds, or for a time period in the range of from about 60 seconds to about 120 seconds, or for a time period greater than about 120 seconds. Furthermore, the non-thermal plasma may have an intensity in the range of from about 2 $J/cm^2$ to about 6 $J/cm^2$ or in the range of from about 6 $J/cm^2$ to about 10 $J/cm^2$. In certain embodiments, the cell population may be ex vivo tissue, such as, for example, an organ.

Additional aspects of the present invention are directed to methods comprising: contacting an ex vivo tissue containing endothelial cells with a non-thermal plasma to control the proliferation of the endothelial cells within the tissue. The non-thermal plasma is an atmospheric pressure dielectric barrier discharge. The tissue may be contacted with the non-thermal plasma directly, indirectly, or separately. In certain embodiments, the endothelial cell proliferation results in an increase in endothelial cells within the tissue by at least 50%, by at least 100%, or by at least 200%. The tissue may be contacted with the non-thermal plasma for various amounts of time. For example, in some embodiments, the endothelial cells are contacted with the non-thermal plasma for about 30 seconds or less, or for about 15 seconds or less. The non-thermal plasma has an intensity in the range of from about 0.5 $J/cm^2$ to about 6 $J/cm^2$. In certain embodiments, the ex vivo tissue may be an organ.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Other features of the subject matter are described below.

BRIEF DESCRIPTION OF THE DRAWINGS

The foregoing and other aspects of the present invention will become apparent from the following detailed description of the invention when considered in conjunction with the accompanying drawings. For the purpose of illustrating the invention, there is shown in the drawings embodiments that are presently preferred, it being understood, however, that the invention is not limited to the specific instrumentalities disclosed. The drawings are not necessarily drawn to scale. In the drawings:

FIG. 1C shows exemplary operating parameters of the non-thermal dielectric barrier discharge (DBD) plasma;

DETAILED DESCRIPTION OF ILLUSTRATIVE EMBODIMENTS

Figure 1A:
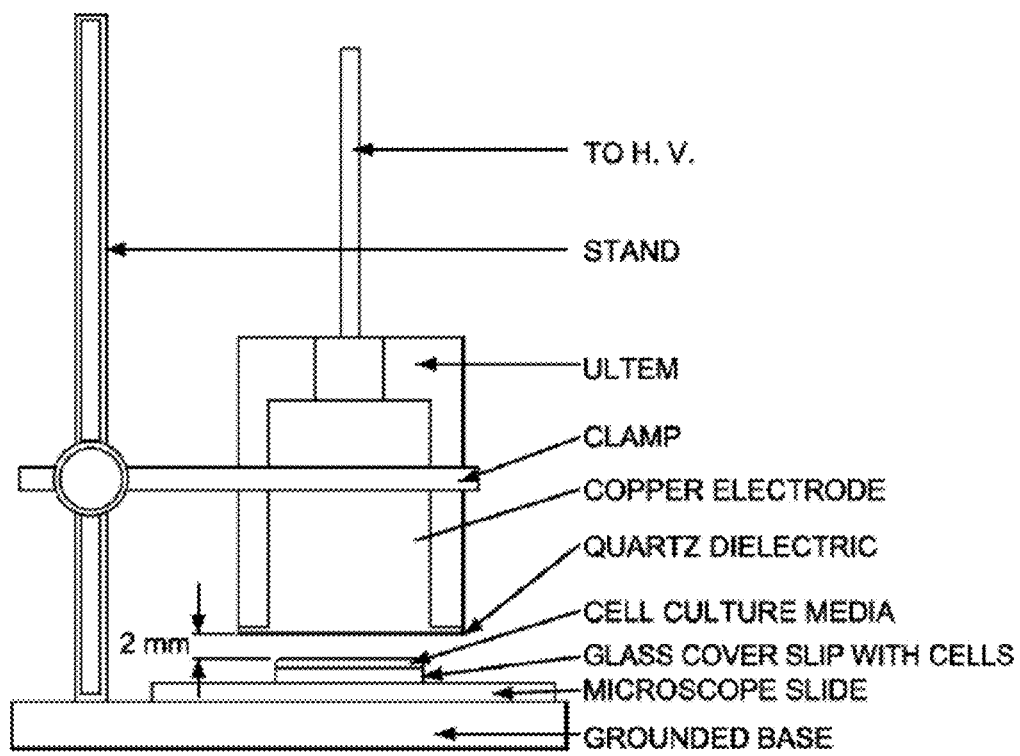
FIG. 1A is a schematic of the experimental setup showing the high voltage electrode and the sample holder.

The present subject matter may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention.

Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Plasmas, referred to as the "fourth state of matter," are partially ionized gases with a certain number of electrons that are not bound to atoms or molecules. In recent years, plasmas have become of significant interest to researchers in fields such as organic and polymer chemistry, fuel conversion, hydrogen production, environmental chemistry, biology, and medicine, among others. This is, in part, because plasmas offer several advantages over traditional chemical processes. For example, plasmas can generate much higher temperatures and energy densities than conventional chemical technologies; plasmas are able to produce very high concentrations of energetic and chemically active species; and plasma systems can operate far from thermodynamic equilibrium, providing extremely high concentrations of chemically active species while having gas temperature as low as room temperature.

Many details concerning the generation and applications of plasmas are described in PLASMA CHEMISTRY (2008), by Fridman.

Plasmas are generated by ionizing gases using any of a variety of ionization sources. Depending upon the ionization source and the extent of ionization, plasmas may be characterized as either thermal or non-thermal. Thermal and non-thermal plasmas can also be characterized by the temperature of their components. Thermal plasmas are in a state of thermal equilibrium, that is, the temperature of the free electrons, ions, and heavy neutral atoms are approximately the same. Non-thermal plasmas, or cold plasmas, are far from a state of thermal equilibrium; the temperature of the free electrons is much greater than the temperature of the ions and heavy neutral atoms within the plasma.

The initial generation of free electrons may vary depending upon the ionization source. With respect to both thermal and non-thermal ionization sources, electrons may be generated at the surface of the cathode due to a potential applied across the electrode. In addition, thermal plasma ionization sources may also generate electrons at the surface of a cathode as a result of the high temperature of the cathode (thermionic emissions) or high electric fields near the surface of the cathode (field emissions).

The energy from these free electrons may be transferred to additional plasma components, providing energy for additional ionization, excitation, dissociation, etc. With respect to non-thermal plasmas, the ionization process typically occurs by direct ionization through electron impact. Direct ionization occurs when an electron of high energy interacts with a valence electron of a neutral atom or molecule. If the energy of the electron is greater than the ionization potential of the valence electron, the valence electron escapes the electron cloud of the atom or molecule and becomes a free electron according to:

$$e^- + A \rightarrow A^+ + e^- + e^-.$$

As the charge of the ion increases, the energy required to remove an additional electron also increases. Thus, the energy required to remove an additional electron from $A^+$ is greater than the energy required to remove the first electron from A to form $A^+$. A benefit of non-thermal plasmas is that because complete ionization does not occur, the power of the ionization source can be adjusted to increase or decrease ionization. This ability to adjust the ionization of the gas provides for a user to "tune" the plasma to their specific needs.

An exemplary thermal plasma ionization source is an arc discharge. Arc discharges have been otherwise used for applications such as metallurgy, metal welding and metal cutting and are known per se. Arc discharges are formed by the application of a potential to a cathode. Arc discharges are characterized by high current densities and low voltage drops. Factors relevant to these characteristics are the usually short distance between the electrodes (typically a few millimeters) and the mostly inert materials of the electrodes (typically, carbon, tungsten, zirconium, silver, etc). The majority of electrons generated in arc discharges are formed by intensive thermionic and field emissions at the surface of the cathode. That is, a much larger number of the electrons are generated directly from the cathode as opposed to secondary sources such as excited atoms or ions. Because of this intense generation of electrons at the cathode, current at the cathode is high, which leads to Joule heating and increased temperatures of the cathodes. Such high temperatures can result in evaporation and erosion of the cathode. The anode in arc discharges may be either an electrode having a composition identical or similar to the cathode or it may be another conductive material. For example, the anode in arc discharges used in metal welding or cutting is the actual metal be welded or cut. Typical values for parameters of thermal arc discharges can be seen in Table 1:

TABLE 1

Arc Discharge Parameters

| Parameters of a Thermal Arc Discharge | Typical Values |
|---|---|
| Gas Pressure | 0.1 to 100 atm |
| Arc Current | 30 A to 30 kA |
| Cathode Current Density | $10^4$ to $10^7$ A/cm$^2$ |
| Voltage | 10 to 100 V |
| Power per unit length | 1 to 10 kW/cm |
| Electron Density | $10^{15}$ to $10^{19}$ cm$^{-3}$ |
| Gas Temperature | 1 to 10 eV |
| Electron Temperature | 1 to 10 eV |

Although thermal plasmas are capable of delivering extremely high powers, they have several drawbacks. In addition to the electrode erosion problems discussed above, thermal plasmas do not allow for adjusting the amount of ionization, they operate at extremely high temperatures, and they lack efficiency.

Non-thermal plasma ionization sources have alleviated some of the above-mentioned problems. Exemplary ionization sources for non-thermal plasmas include glow discharges, gliding arc discharges, and floating electrode dielectric barrier discharges, among others. In contrast to thermal plasmas, non-thermal plasmas provide for high selectivity, high energy efficiencies, and low operating temperatures. In many non-thermal plasma systems, electron temperatures are about 10,000K while the bulk gas temperature may be as low as room temperature.

Dielectric barrier discharge plasmas (DBD) may be generated using an alternating voltage at frequencies ranging from about 0.5 kHz to about 500 kHz between a high voltage electrode and a ground electrode. In addition, one or more dielectric barriers are placed between the electrodes. DBD occurs at atmospheric pressure in air or other gases when sufficiently high voltage of sinusoidal waveforms or short duration pulses are applied between two electrodes, with at least one of the electrodes being insulated. DBDs have been employed for over a century and have been used for the generation of ozone in the purification of water, polymer treatment (to promote wettability, printability, adhesion), and for pollution control. DBDs prevent spark formation by limiting current between the electrodes.

Several materials can be utilized as the dielectric barrier. These include glass, quartz, and ceramics, among others. The clearance between the discharge gaps typically ranges from about 0.1 mm and several centimeters. The required voltage applied to the high voltage electrode varies depending upon the pressure and the clearance between the discharge gaps. For a DBD at atmospheric pressure and a few millimeters between the gaps, the voltage required to generate a plasma is typically about 10 kV. The insulator between the electrodes prevents the build-up of high current. As a result, the discharge creates electrically safe plasma without substantial gas heating.

Non-thermal atmospheric pressure dielectric barrier discharge plasma has emerged as a novel tool in medicine. This non-thermal plasma enables many new medical applications including living tissue sterilization, blood coagulation, apoptosis induction in malignant cells, cell attachment modulation, and wound healing, among others.

Aspects of the present invention are directed to methods comprising contacting an endothelial cell in an endothelial cell population with a non-thermal plasma. Upon contact with the non-thermal plasma, the cell may release an angiogenic growth factor, and the angiogenic growth factor may induce endothelial cell proliferation. Endothelial cells line all blood contacting surfaces in the body and under certain circumstances may release an angiogenic growth factor, which in conjunction with many other signals may induce endothelial cells to invade the surrounding tissue, proliferate, and develop into new blood vessels. In certain embodiments, the angiogenic growth factor is fibroblast growth factor-2 (FGF2). FGF2, in conjunction with other cell signaling pathways, may induce endothelial cell proliferation to develop into new blood vessels.

As used herein, the term "endothelial cell population" refers to a group of at least two endothelial cells. In certain embodiments, the endothelial cell population is in vitro, while in other embodiments, the cell population is in vivo. In one embodiment, an endothelial cell population may be an endothelial cell monolayer on a glass substrate. In another embodiment, an endothelial cell population may be endothelial cells in tissue in vivo or ex vivo, such as, for example, in explanted tissue. In yet another embodiment, an endothelial cell population may be part of a three-dimensional in vitro model.

Preferably, the non-thermal plasma is an atmospheric pressure dielectric barrier discharge (DBD) plasma. The DBD may be operated at a microsecond pulse rate, with a voltage in the range of from about 10 kV to about 30 kV, preferably in the range of from about 15 kV to about 25 kV, more preferably at about 20 kV. The pulse width may be in the range of from about 0.5 microseconds ($\mu$s) and 5 $\mu$s, preferably in the range of from about 1 $\mu$s and 3 $\mu$s, most preferably in the range of from about 1.5 $\mu$s and 2 $\mu$s. The frequency of the DBD may be in the range of from about 0.1 kHz to about 5 kHz, preferably in the range of from about 0.2 kHz to about 2 kHz, most preferably in the range of from about 0.5 kHz to about 1.5 kHz. The power density of the DBD may be in the range of from about 0.05 W/cm$^2$ to about 5 W/cm$^2$, preferably in the range of from about 0.08 W/cm$^2$ to about 1.2 W/cm$^2$, more preferably in the range of from about 0.1 W/cm$^2$ to about 1 W/cm$^2$. The rotational temperature may be in the range of from about 200K to about 400K, preferably in the range of from about 300K to about 350K. The vibrational temperature may be in the range of from about 2000K to about 5000K, preferably in the range of from about 3000 to about 4000K.

Upon contact with the non-thermal plasma, endothelial cells may release an angiogenic growth factor, which may induce cell proliferation. Preferably, the angiogenic growth factor is FGF2. Although not intending to be limited to any particular theory, it is thought that cell proliferation occurs when the cell is sub-lethally damaged. Such sub-lethal damage disrupts the cell membrane and the angiogenic growth factor, for example, FGF2, is released from the cell. Because FGF2 has no signal sequence for secretion, it is thought that it is primarily released during sub-lethal cell membrane damage.

The membrane of an endothelial cell can be sub-lethally damaged by contact with non-thermal plasma. Whether a cell is sub-lethally damaged or killed is dependent upon, for example, the intensity of the non-thermal plasma and the exposure time of the endothelial cell to the plasma. Cells treated with plasma for too long die and no proliferation occurs. In one embodiment, cell proliferation occurs with a treatment time of about 30 seconds or less. In another embodiment, cell proliferation occurs with a treatment time of about 15 seconds or less. Depending upon the length of treatment, the amount of proliferation may vary. For example, proliferation may result in an increase in the cell population by at least about 25 percent, or at least about 50 percent, or at least about 75 percent. Preferably, the size of the population increases by at least about 100 percent or at least about 200 percent.

The amount of proliferation may also depend upon the intensity of the non-thermal plasma. For example, in some embodiments, proliferation occurs with a non-thermal plasma intensity in the range of from about 1 to about 8 J/cm$^2$. In another embodiment, the intensity of the non-thermal plasma may in the range of from about 2 to about 6 J/cm$^2$, preferably in the range of from about 3 to about 5 J/cm$^2$.

The extent of proliferation may also depend upon the plasma components that contact the endothelial cell. A plasma discharge contains various species including neutral reactive species, charged particles, such as ions, and electrons. In certain embodiments, the non-thermal plasma may modify the medium in which the cells are treated. Species in this modified medium may subsequently interact with the cells. For example, active neutral species or charged particles may modify the medium being treated by producing reactive oxygen species (ROS). ROS may be separated into long living ROS and short living ROS. Long living ROS include, for example, $O_3$, NO, $HO_2$, and $H_2O_2$, among others. Short living ROS include, for example, OH, O, electrically excited O, and $O_2$, among others. Such ROS may induce cells to release FGF2 by sub-lethal lipid peroxidation or through some other transport mechanism through the cell membrane and affecting the expression and production of FGF2 intracellularly. In other embodiments, these ROS may immediately interact with the medium and medium components such as, for example, amino acids, proteins, and glucose, leading to production of long living reactive organic hydroperoxides. These long living reactive protein and amino acid hydroperoxides may induce cell membrane damage leading to lipid peroxidation or alter intracellular signaling pathways activated by binding to the cell membrane receptors leading to an increase in the expression of intracellular FGF2 and finally leading to release of FGF2 from endothelial cells. In one embodiment, plasma treatment induces membrane damage in a certain population of cells being treated. These cells may subsequently release intracellular contents of membrane bound growth factors, such as, for example FGF2

The endothelial cell can be contacted with the non-thermal plasma in a variety of ways. In certain embodiments, the cells are contacted by the non-thermal plasma by direct contact. "Direct contact" refers to when the cell is directly contacted with the entire plasma discharge, that is, neutral reactive species, charge particles, such as ions, and electrons. Direct contact may permit a flux of various active short living and long living neutral species of atoms and molecules as well as UV radiation to the surface of the living tissue. A distinguishing feature of the direct plasma treatment is that a significant flux of charges reaches the surface of the living tissue. These charges may consist of both electrons as well as positive and negative ions like super oxide radicals. In another embodiment, the cell is indirectly contacted with the non-thermal plasma. "Indirect contact" refers to when the cell is contacted with mostly neutral atoms and involves small, if any, flux of charges to the surface of the living tissue. With indirect treatment, the active uncharged species are typically delivered to the surface via flow of gas through a plasma region. In certain embodiments, indirect contact is achieved by using a grounded mesh to block charged particles from contacting the cell. In another embodiment, a "separated" configuration is used to contact the cell with the non-thermal plasma. "Separated" refers to when a media is treated with the non-thermal and the media is then applied to cells. In this embodiment, short-lived reactive species do not contact the cell.

Both indirect and direct non-thermal plasma treatments permit tuning of the plasma properties. For example, the ratio of NO to ozone produced in plasma can be tuned. It is also possible to tune the micro-structure of the plasma. The fact that direct plasma treatment involves substantial charge flux provides greater flexibility in tuning the non-thermal plasma effects. Indirect plasma treatment, on the other hand, may have an advantage when the plasma device needs to be at a substantial distance from the surface. Separated contact may be suitable for situations where cells are inaccessible to direct or indirect plasma contact.

Contacting endothelial cells with a non-thermal plasma is useful for the treatment of various diseases. For example, endothelial cells play a major role in angiogenesis, the growth of new blood vessels from existing vessels. Endothelial cells produce angiogenic growth factors such as FGF2, which in conjunction with other cell signaling pathways induce endothelial cell proliferation, to develop into new blood vessels. In varied disease conditions like diabetic wounds or cancer, healing may result from promoting or inhibiting angiogenesis. Depending upon the disease, angiogenesis can be either beneficial or destructive. In wound healing, it is believed that angiogenesis is required at the wound site for rapid healing, whereas in cancer, inhibition of angiogenesis can starve a tumor and prevent its growth. Non-thermal plasma treatment dose can be varied to grow or regress blood vessels. Short exposures to low power non-thermal plasma may induce significant proliferation in endothelial cells as compared to control. Such treatment may be useful in treating wounds like diabetic ulcers by promoting angiogenesis and thereby achieving faster healing without damaging the surrounding tissue. On the other hand, long exposures to low power non-thermal plasma or short exposures to high power plasma may significantly inhibit endothelial cell proliferation by inducing apoptosis. This may be beneficial for treating cancer by suppressing angiogenesis without an adverse inflammatory response.

In certain embodiments of the present invention, ex vivo tissue may be treated with non-thermal plasma to promote blood vessel growth. Representative tissues that may be transplanted include bone tissue, bone marrow, tendons, cornea, heart valves, veins, and skin. This may be of particular use in organ transplants, wherein an organ removed from one individual may be treated with a non-thermal plasma prior to implantation into another individual. Such treatment may assist in incorporating the organ into the new body. Representative organs that may be transplanted include for example, heart, kidney, liver, lung, pancreas, eyes and intestine.

One aspect of the present invention is directed to a method for treating a disease comprising promoting angiogenesis by contacting an endothelial cell in an endothelial cell population with a non-thermal plasma. Upon contact with the non-thermal plasma, the endothelial cell may release an angiogenic growth factor. The angiogenic growth factor may induce endothelial cell proliferation. Preferably, the angiogenic growth factor is FGF2 and the non-thermal plasma is an atmospheric pressure dielectric barrier plasma. The endothelial cells may be contacted with non-thermal plasma directly, indirectly, or separately.

In certain embodiments, the endothelial cell proliferation results in an increase in the cell population by at least 50%. In other embodiments, the endothelial cell proliferation results in an increase in the cell population by at least 100%. In still other embodiments, the endothelial cell proliferation results in an increase in the cell population by at least 200%.

Under certain conditions, the number of endothelial cells in an endothelial cell population may be decreased by contacting an endothelial cell in an endothelial cell population with a non-thermal plasma. In these instances, apoptosis occurs due to an increase in the amount of time the endothelial cell has been exposed to the non-thermal plasma or an increased intensity of the non-thermal plasma. In certain embodiments, apoptosis occurs after an exposure time of about 30 seconds. In certain embodiments, apoptosis occurs during an exposure time in the range of from about 30 to about 60 seconds. In other embodiments, exposure occurs in the range of from about 60 to about 120 seconds. In other embodiments, apoptosis occurs at an exposure time of about 120 second or more. The percentage of viable cells decreases with longer exposures over 30 seconds. For example, in one embodiment, the number of viable cells is reduced in the range of from about 10 to about 75 percent. In another embodiment, the number of viable cells is reduced in the range of from about 25 to about 50 percent.

As with cell proliferation, cell apoptosis may occur when endothelial cells are contacted with the non-thermal plasma either directly, indirectly, or separately. Apoptosis may also occur due to an increased intensity in the non-thermal plasma. For example, the intensity of the non-thermal plasma may be in the range of from about 6 $J/cm^2$ to about 10 $J/cm^2$, or, for example, in the range of from about 10 $J/cm^2$ to about 20 $J/cm^2$, or, for example, greater than about 20 $J/cm^2$.

The present invention is further defined in the following Examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Endothelial Cell Culture

Porcine aortic endothelial cells (PAEC) were maintained in low glucose Dulbecco's Modified Eagle's Medium (DMEM) (Cellgro, Mediatech, VA, USA) supplemented with 5% fetal bovine serum (Hyclone, UT, USA), 1% L-glutamine, and 1% penicillin-streptomycin (GIBCO, Invitrogen, CA, USA). Media was changed every two days. For plasma treatment, cells were washed with phosphate buffered saline, detached with 0.1% trypsin (GIBCO, Invitrogen, CA, USA), and seeded near confluence ($4 \times 10^5$ cells/well) on 18 mm diameter glass cover slips (VWR, PA, USA) in 12-well plates (Corning Costar, NY, USA). Cells were cultured for 24 hours prior to plasma treatment in 1.5 ml supplemented media in a 37° C., 5% $CO_2$ incubator to allow full attachment and spreading.

Porcine tumor necrosis factor-α (TNF-α) was from R&D Systems (Minneapolis, Minn.). Recombinant human FGF2 was from Peprotech, and the neutralizing FGF2 antibody was from Upstate Biotechnology (Lake Placid, N.Y.). N-Acetyl-L-cysteine (2 mM, Sigma-Aldrich, St Louis, Mo.), an intracellular reactive oxygen species (ROS) scavenger and sodium pyruvate (10 mM, Sigma-Aldrich, St Louis, Mo.), an extracellular ROS scavenger were used to block the reactive oxygen species produced by non-thermal plasma treatment.

Example 2

Endothelial Cell Plasma Treatment

Figure 1B:
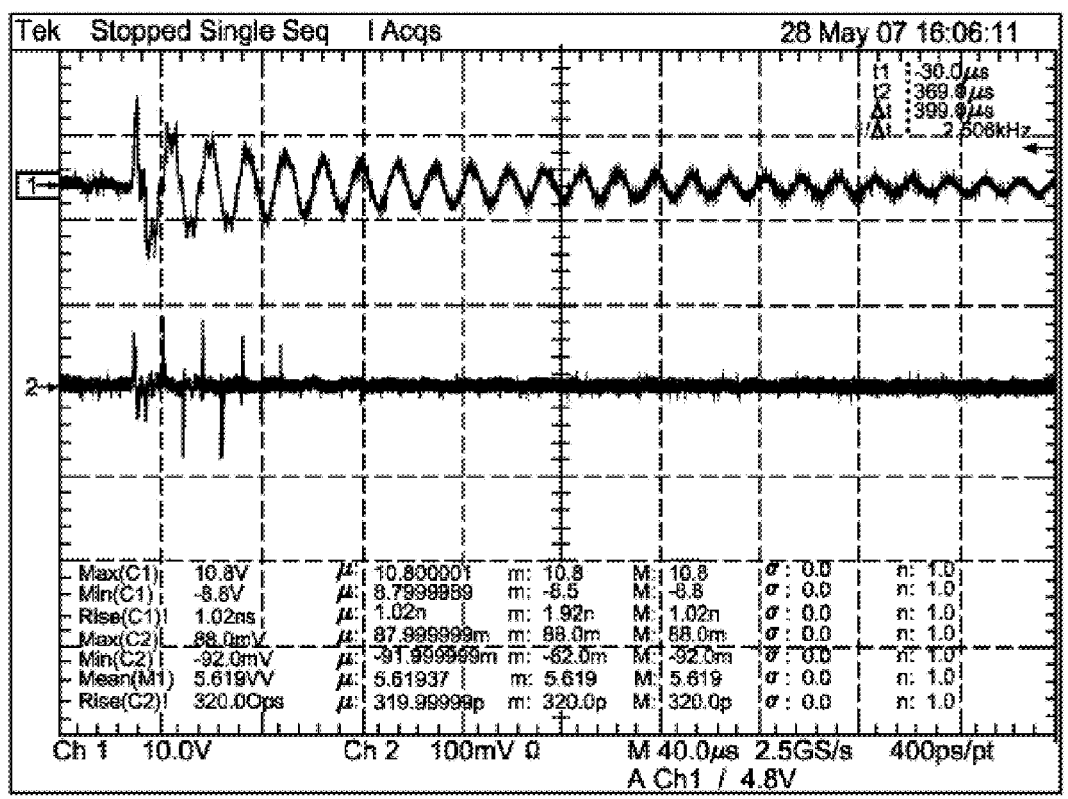
FIG. 1B is a graphical representation of waveforms for the voltage (top) and current (bottom) pulses.

Non-thermal atmospheric pressure dielectric barrier discharge plasma was produced using an experimental setup shown in FIG. 1A. The non-thermal plasma was generated by applying alternating polarity pulsed (500 Hz-1.5 kHz) voltage of ~20 kV magnitude (peak to peak) between the insulated high voltage electrode and the sample undergoing treatment using a variable voltage and variable frequency power supply (Quinta, Russia). 1 mm thick, polished clear fused quartz was used as an insulating dielectric barrier covering the 1 inch diameter copper electrode. The discharge gap between the bottom of the quartz and the treated sample surface was fixed at 2 mm. The pulse waveform of a 20 kV, 1.65 μs, with a rise time of 5 V/ns is shown in FIG. 1B. Discharge power density was measured to be roughly 0.13 Watts/cm$^2$ (at 500 Hz) and 0.31 Watts/cm$^2$ (at 1.5 kHz) using both electrical characterization and a specially designed calorimetric system.

PAEC on glass cover slips were exposed to low power plasma for times ranging from 5 to 120 seconds. Briefly, each cover slip was removed from the 12-well plate and placed on a microscope slide, which was then positioned on the grounded base of the plasma device. 50 μl of serum free media was added to the glass cover slip before plasma treatment to prevent sample drying. Following plasma treatment, the cover slip was immediately placed in a new 12-well plate, 1.5 ml of supplemented media was added to the well, and the samples were returned to the incubator.

Three different approaches were used for non-thermal plasma-treatment of cells in vitro: direct, indirect and separated. In direct treatment, the sample itself was one of the electrodes that created the plasma discharge, as illustrated in FIGS. 1A and 19. Plasma discharge occurred between the powered high voltage electrode quartz surface and the sample surface, which exposed the sample directly to both neutral reactive species and charged particles. In contrast, for indirect treatment, a grounded mesh was placed between the high voltage electrode and the treated sample to prevent charged particles from reaching the sample surface. In separated plasma treatment, medium alone was plasma treated separately from cells and then immediately applied to cells. In this case, cells were not in direct contact with any plasma component.

Example 3

Non-Thermal Plasma-Induced Cell Death

Non-thermal plasma endothelial cell cytotoxicity was measured via cell counts and a Live/Dead assay. For cell counts, PAEC were plasma treated as described previously. At 3 and 24 hours following plasma treatment, attached (live) cells were trypsinized and counted using a Coulter counter (Beckman Coulter, CA, USA). For the Live/Dead assay, at 3 and 24 hours post treatment, cell viability was assessed with a Live/Dead Viability/Cytotoxicity Assay (Molecular Probes, Invitrogen, CA) as per manufacturer instructions. Briefly, cells were labeled with 1 μM ethidium homodimer and 0.25 μM calcein, incubated at room temperature for 45 minutes, and imaged by fluorescent microscopy (Olympus, USA) with a digital high performance CCD camera (SPOT microscope digital camera, Diagnostic Instruments, MI, USA). Live cells convert cell-permeant calcein to a FITC fluorescent form via intracellular esterase activity, whereas cell impermeant ethidium homodimer binds to nucleic acids in membrane damaged dead cells to enhance TRITC fluorescence. Green and red images were combined using Spot Advanced software (Diagnostic Instruments, MI, USA), and dead cells were manually counted in Adobe Photoshop (Adobe, CA, USA) in five distinct sample areas.

Endothelial cell apoptosis was measured via annexin V-propidium iodide labeling. Annexin V binds phosphatidylserine translocated from the inner to the outer cell membrane. Cells in early apoptosis are identified as annexin V-positive and negative for the vital dye propidium iodide, which is membrane impermeant and excluded from viable cells. Endothelial cells were prepared for the annexin V-propidium iodide assay by combining floating and trypsin-released attached cells. Samples were centrifuged to pellet cells, washed thoroughly, resuspended in annexin binding buffer, and labeled with annexin V-fluorescein and propidium iodide as per manufacturer instructions (BD Pharmingen, San Jose, Calif.). Samples were analyzed immediately by flow cytometry (BD FACS Canto).

Example 4

Endothelial Cell Membrane Damage and FGF2 Release

Endothelial cell membrane damage following non-thermal plasma treatment was quantified through lactase dehydrogenase (LDH) release. PAEC on cover slips were plasma treated as described, however DMEM without sodium pyruvate was used for all LDH assays since sodium pyruvate interfered with the LDH assay. Tumor necrosis factor-α (TNF-α 10 ng/ml) was the positive control. 0.5 ml of conditioned media was collected at 2, 4, 6, 8, 12 and 24 h after plasma treatment, and LDH was quantified using the Cyototox-ONE Homogeneous Membrane Integrity Assay (Promega, WI, USA) as per manufacturer instructions.

FGF2 release from plasma treated cells was measured by enzyme linked immunosorbent assay (ELISA). PAEC were plasma treated and then placed in 1.5 ml serum-free DMEM. At times ranging from 0.5 to 24 h after plasma treatment, media samples were collected without disturbing cells and centrifuged to remove dead floating cells. FGF2 levels in media samples were quantified via FGF ELISA (R&D Systems, MN, USA) as per manufacturer instructions.

Example 5

Non-Thermal Plasma Induced Cell Proliferation

Endothelial cell proliferation was measured through cell counts and BrdU incorporation either on directly treated cells or through a conditioned media assay. For the conditioned media assay, confluent PAEC on cover slips were plasma treated as described. Cells were then transferred to new 12-well plates and incubated for 3 h in 1 ml serum-free DMEM. Following this incubation, the conditioned media from plasma-treated cells was collected and centrifuged at 5000 rpm for 5 minutes to remove dead cells. 0.5 ml conditioned media, along with 1 ml supplemented media, was added to subconfluent PAEC (10,000 cells/well) on days 2, 4, and 6 and cell proliferation was assessed. Conditioned media from untreated cells, as well as serum-free media alone, were used as controls. FGF2 effects were blocked using an FGF2 neutralizing antibody (10 μg/ml), which was pre-incubated for 30 min with the conditioned media prior to adding it to cells.

For cell counts, 10,000 PAEC were seeded on 18 mm diameter cover slips in 12-well plates. Cells were plasma treated as described and incubated for an additional 7 days with a media change on days 2, 4 and 6. Cell number was quantified on days 1, 3, 5 and 7 by counting trypsin-detached cells using a Coulter counter. For directly treated cells, fold proliferation was determined by taking the ratio of cell number on day five to day one.

PAEC proliferation following conditioned media plasma treatment was determined by BrdU incorporation. For BrDU incorporation, 10,000 PAEC were seeded in 96-well plate and incubated in 5% FBS medium. Confluent PAEC on cover slips were plasma treated as described. Cells were then transferred to new 12-well plates and incubated for 3 h in 1 ml serum-free DMEM. Following this incubation, the conditioned media from plasma-treated cells was collected and centrifuged at 5000 rpm for 5 minutes to remove dead cells. 0.5 ml conditioned media, along with 1 ml supplemented media, was added to subconfluent PAEC (10,000 cells/well in 96 well plate) on day 1. The BrdU cell proliferation assay was performed by means of Millipore BrdU cell proliferation assay kit (Chemicon International (Millipore) MA, USA, www.millipore.com) according to the manufacturer's instructions. This assay is based on the incorporation of the thymidine analogue Bromodeoxyuridine (5-bromo-2-deoxyuridine, BrdU) in place of thymidine into newly synthesized DNA of replicating cells by enzyme-linked immunosorbent assay (ELISA). Briefly, following incubation in conditioned medium for 18 h, conditioned medium was removed and 20 μl of BrdU labeling solution was added to each well for 3 h. After 3 h of incubation with BrdU, cells were fixed and incubated with anti-BrdU conjugated with peroxidase. Subsequent to substrate addition, the optical density at 450 nm with a reference wavelength of 570 nm (OD450/570), which was directly proportional to the amount of DNA synthesis, was determined at room temperature using a microplate reader (TECAN, Switzerland)

Example 6

Statistical Analysis

Statistical analyses were performed with Prism software (Graphpad, CA, USA). Data were normally distributed and expressed as the mean±S.D. Comparisons between two groups were analyzed by Student's t test, and comparisons between more than 2 groups were analyzed by ANOVA. A value of p≤0.05 was considered statistically significant and is indicated in the text as such or in figures with a pound sign (#). A value of p≤0.01 is indicated with an asterisk (*).

Example 7

Endothelial Cell FGF2 Release Following Post Plasma Treatment

Figure 4A:
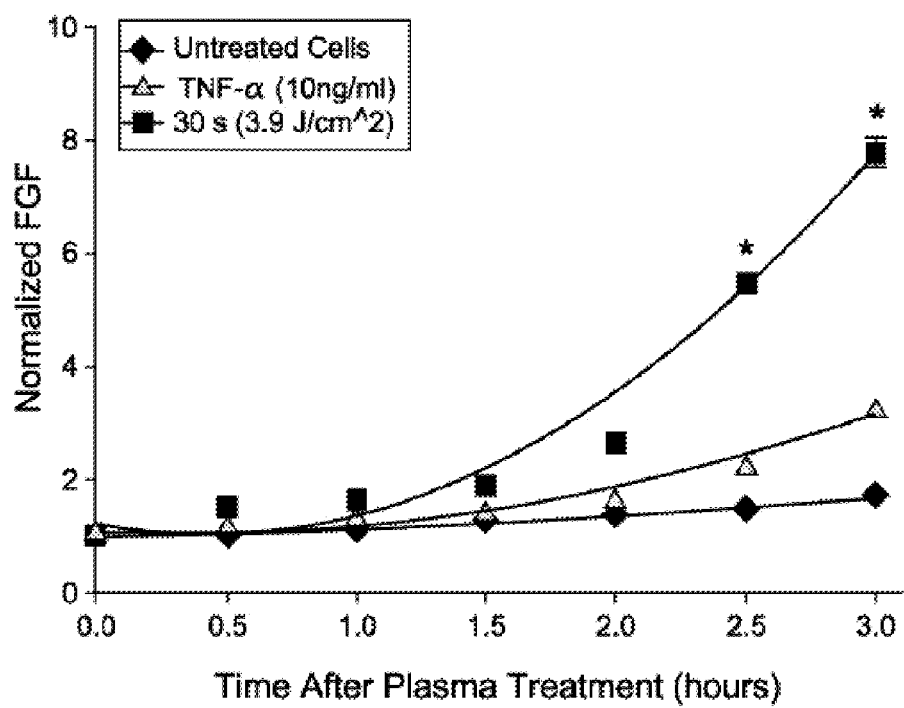
FIG. 4A shows the relationship between the release of FGF2 and the time after plasma treatment.

In certain embodiments, the angiogenic growth factor released from the endothelial cell is FGF2. FGF2 has no signal sequence for secretion, and therefore is primarily known to be released during sub-lethal cell membrane damage. The membrane of the endothelial cell could be sub-lethally damages by contact with the non-thermal plasma. The FGF2 level in the media increased up to 3 h after plasma treatment (3.9 J/cm2, 30 s) and then rapidly decreased up to 24 h after plasma treatment (FIGS. 4a and b). In contrast, FGF2 media levels for cells treated with 10 ng/ml TNF-α as a positive control rose more slowly but continued to rise up to 24 h.

Figure 4B:
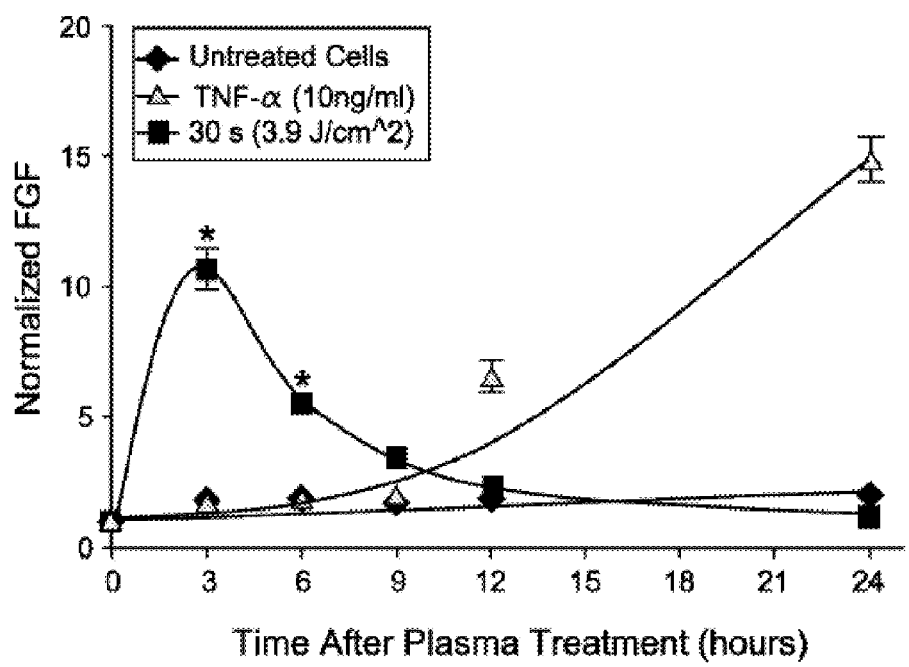
FIG. 4B shows the relationship between the release of FGF2 and the time after plasma treatment.
Figure 4C:
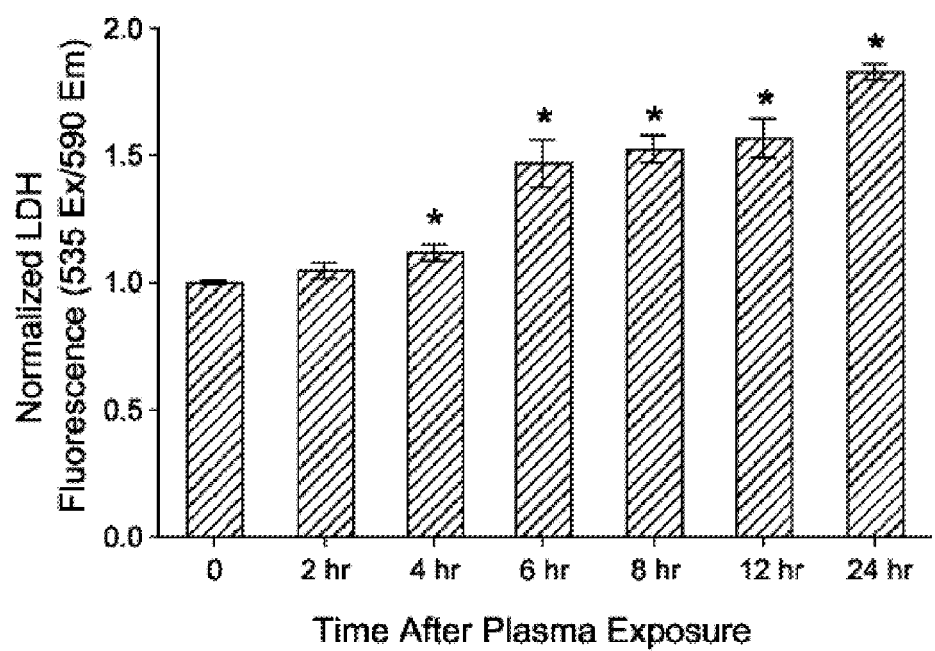
FIG. 4C shows the relationship between the release of FGF2 and the time after plasma treatment.
Figure 4D:
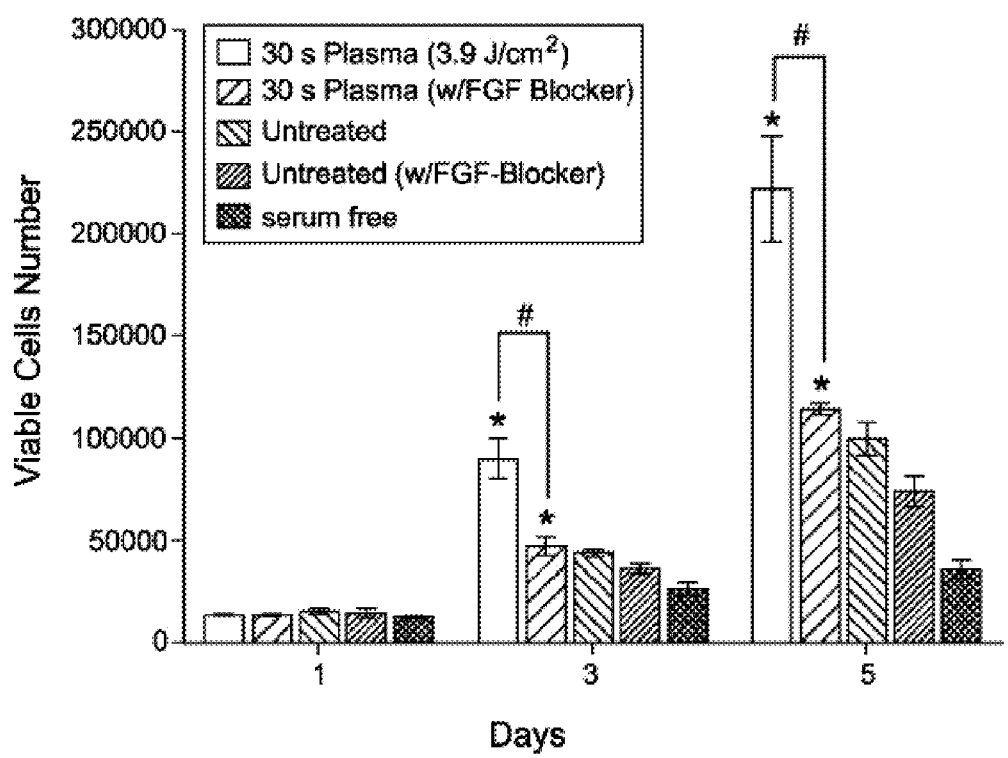
FIG. 4D shows the relationship between the release of FGF2 and the time after plasma treatment.
Figure 5A:
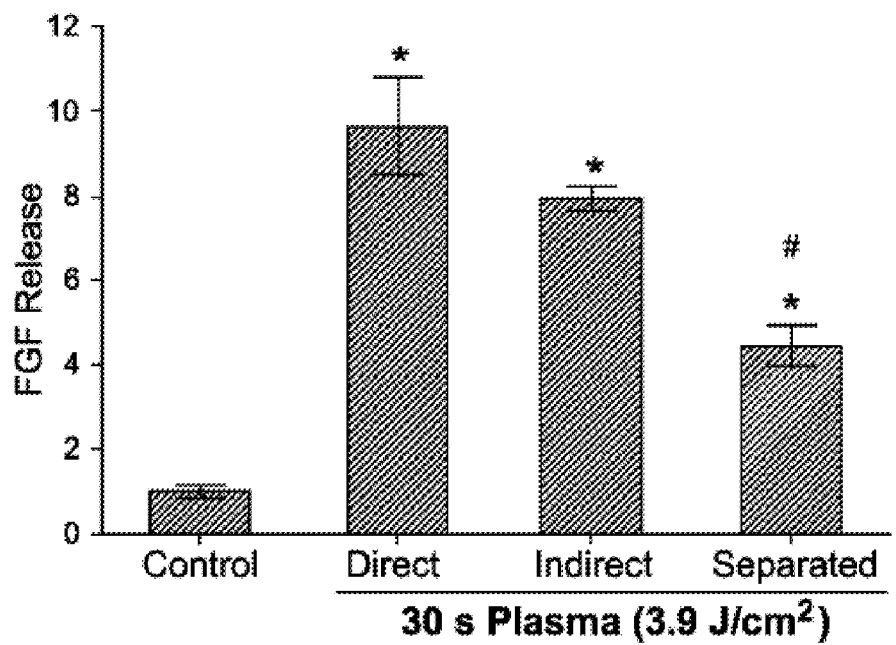
FIG. 5A shows a comparison of different plasma treatment methods with respect to FGF2 release from endothelial cells.
Figure 5B:
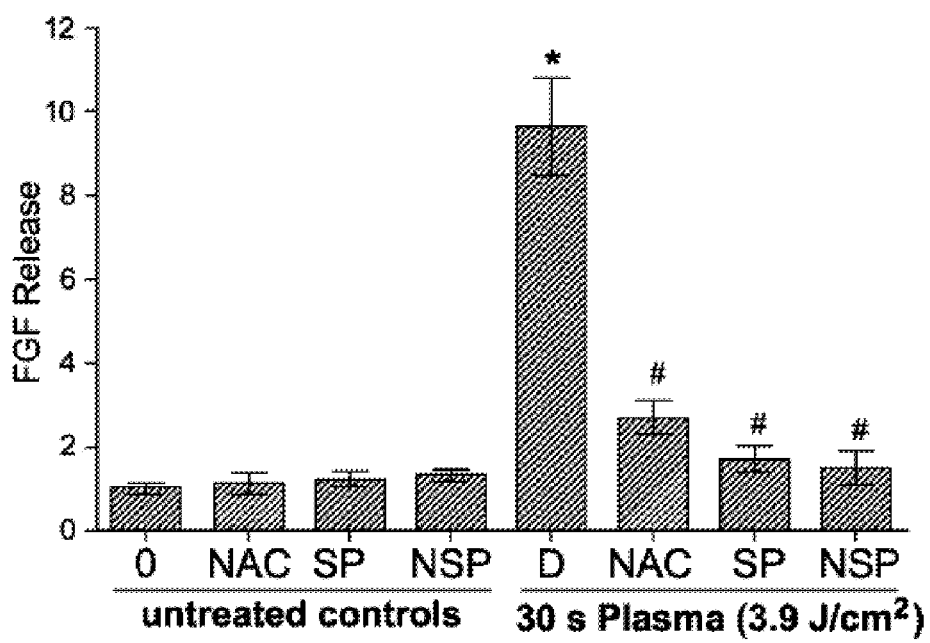
FIG. 5B shows a comparison of different plasma treatment methods with respect to FGF2 release.

To understand the role of plasma-induced injury to the cell membrane in FGF2 release, endothelial cell membrane damage was assessed by LDH release 24 h following plasma treatment. Media LDH level increased significantly by 4 h after plasma treatment and continued to rise throughout the first 24 hours (FIG. 4c, p<0.01 by ANOVA), comparable to the TNF-α positive control. The specific role of released FGF2 in enhanced endothelial cell proliferation by plasma treatment was investigated using an FGF2 neutralizing antibody to block FGF2 effects. The FGF2 neutralizing antibody had no significant effect on cells exposed to untreated cell conditioned medium. However, the FGF2 neutralizing antibody significantly suppressed proliferation in endothelial cells exposed to plasma-treated cell conditioned medium (FIG. 4d). The viable cell number for samples incubated in plasma-treated cell conditioned medium with a neutralizing antibody was similar to samples incubated in untreated cell conditioned medium. These data suggest that cell plasma treatment leads to FGF2 release, and this FGF2 release contributes to the enhanced endothelial cell proliferation following plasma treatment.

Example 8

Endothelial Cell Proliferation in Response to Non-Thermal Plasma Treatment

Figure 2A:
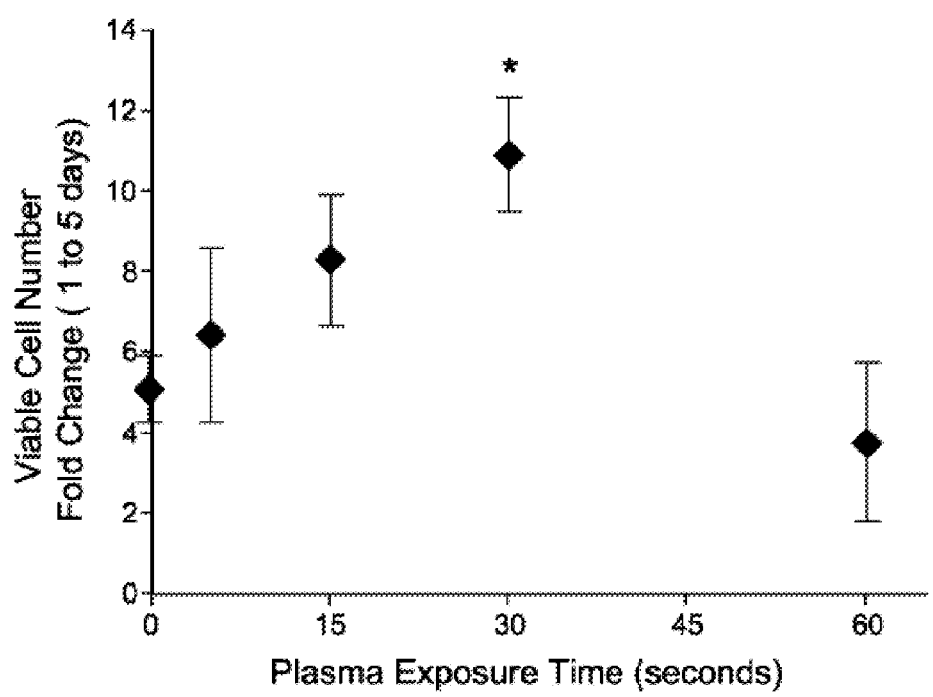
FIG. 2A shows the relationship between endothelial cell proliferation and non-thermal plasma exposure time.
Figure 2B:
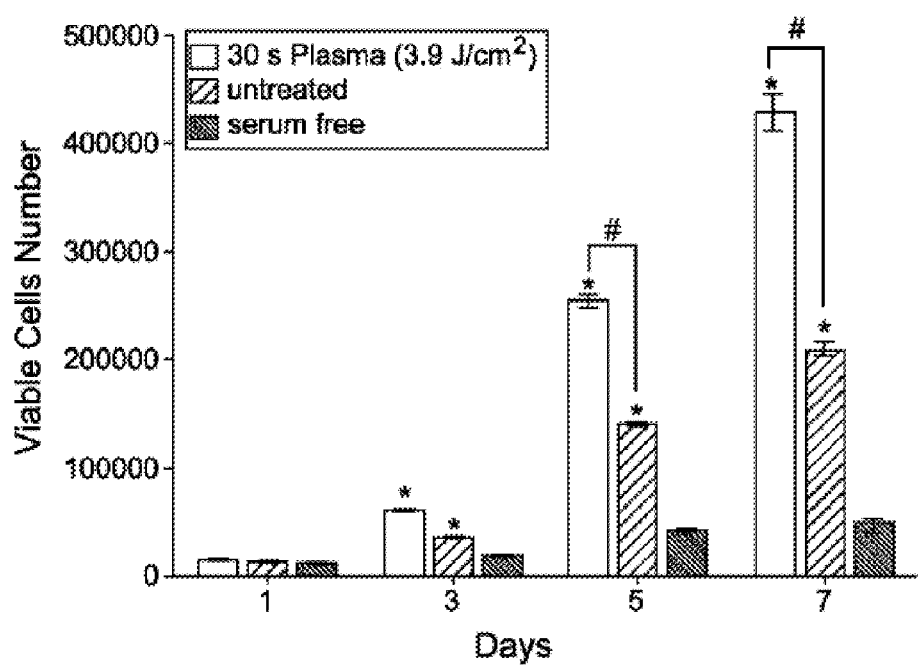
FIG. 2B shows the relationship between endothelial cell proliferation and cell incubation in non-thermal plasma treated conditioned medium seven days after treatment.

Endothelial cell proliferation may be enhanced by low dose non-thermal plasma treatment. Cells treated with plasma showed greater viable cell number than control up to 30 seconds of plasma treatment. With the 30 second treatment, endothelial cells demonstrated twice as many viable cells as untreated controls (FIG. 2A).

However, increased plasma treatment times beyond 30 seconds resulted in decreased cell number. To determine if increased endothelial cell number was related to a soluble factor secreted by the cells, endothelial cells were incubated in conditioned medium from non-thermal plasma treated cells (3.9 J/cm$^2$, 30 s), with conditioned medium from untreated cells or serum free media as controls (FIG. 2A). Plasma treatment dose was selected based on the maximal observed effect in the previous experiment. Viable cell number is twice as higher in cells incubated with plasma-treated cell conditioned medium on days 3, 5 and 7 when compared to cells incubated with untreated cell conditioned medium.

Example 9

Endothelial Cell Death in Response to Non-Thermal Plasma Treatment

Figure 3A:
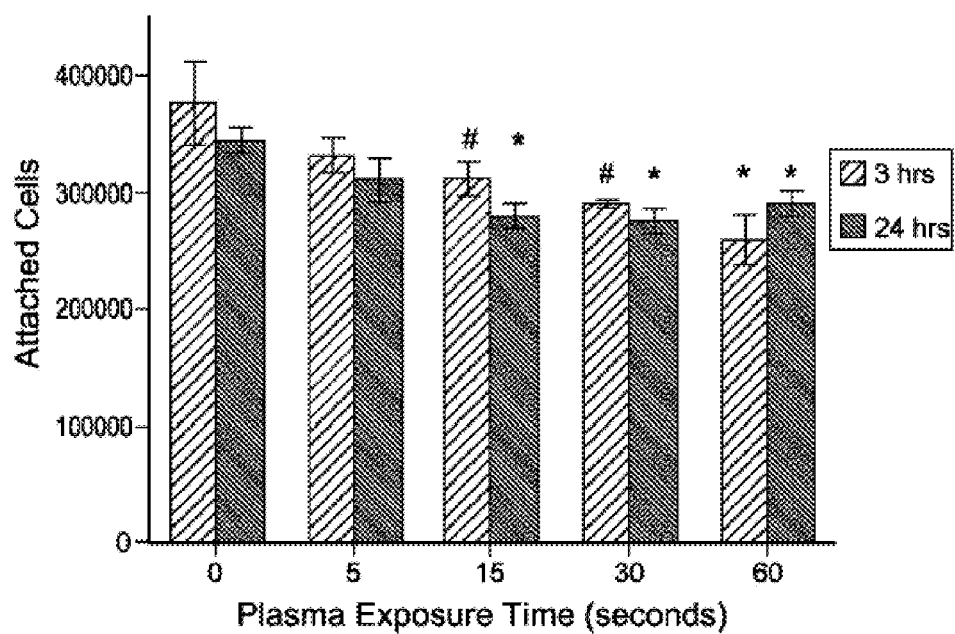
FIG. 3A shows the relationship between the number of live, attached cells and non-thermal plasma exposure time.
Figure 3B:
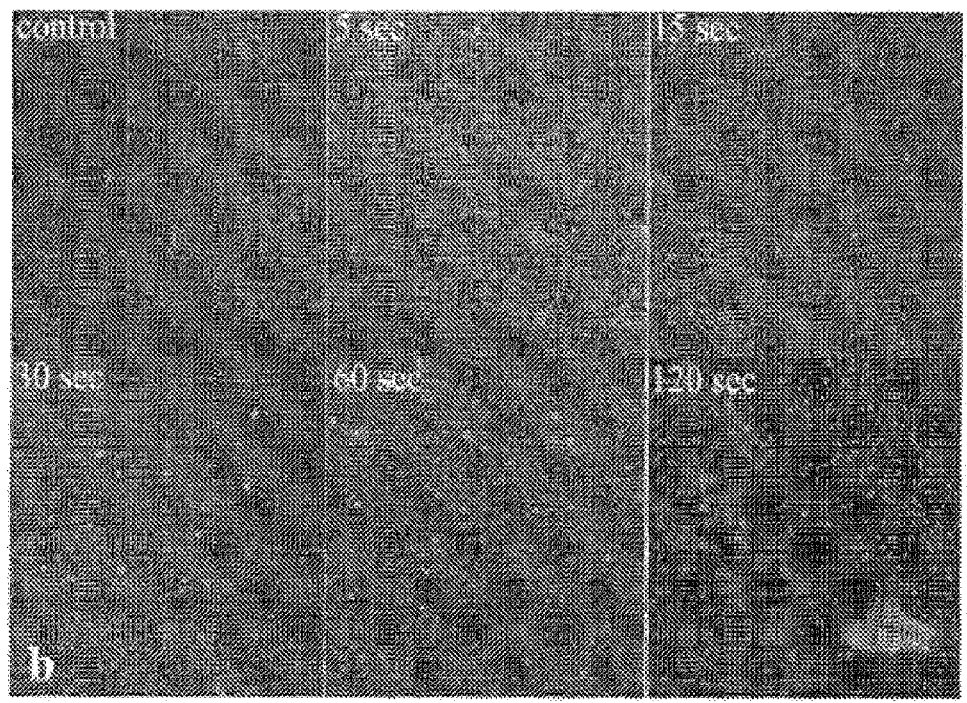
FIG. 3B shows a fluorescent image of dead cells and live cells.
Figure 3C:
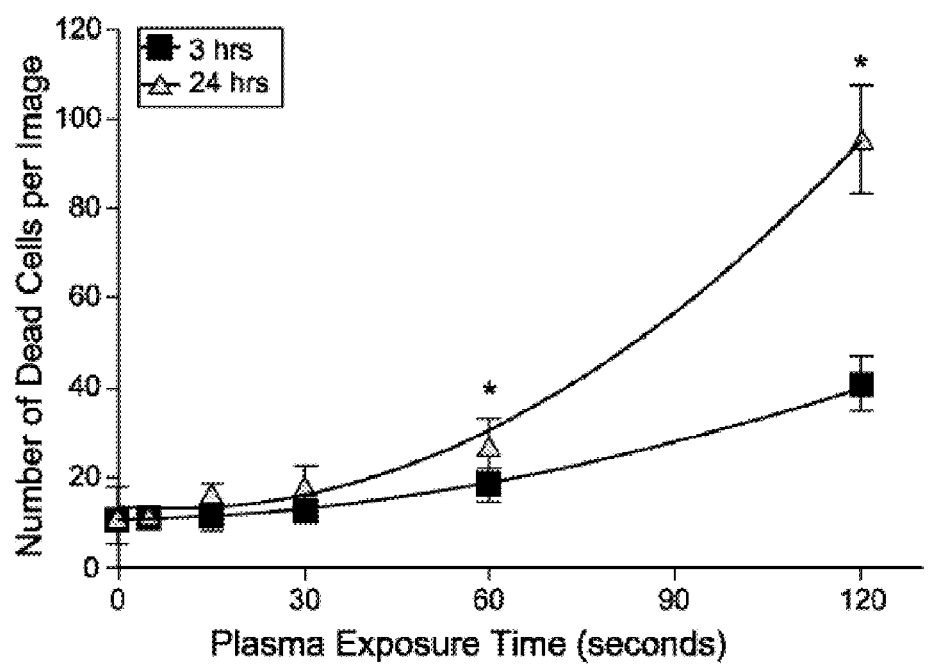
FIG. 3C shows the relationship between the number of dead cells and non-thermal plasma exposure time.
Figure 3D:
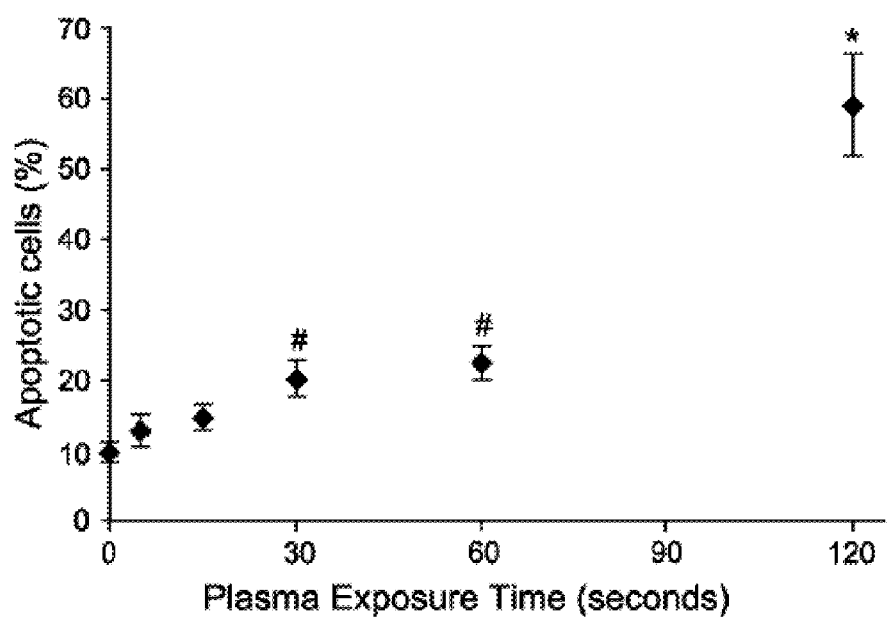
FIG. 3D shows the relationship between the percentage of apoptotic cells and non-thermal plasma exposure time.

Decreased viable cell number may be observed at higher non-thermal plasma treatment levels. Non-thermal plasma may be relatively non-toxic to endothelial cells at exposure times up to 60 seconds. While the number of live, attached cells decreased as plasma exposure time increased, at both three and 24 hours after plasma treatment, more than 75% of endothelial cells remained viable even with 60 s of plasma treatment (FIG. 3A). There was no significant difference between cell viability 3 and 24 hours following plasma exposure for each treatment time, suggesting no long term plasma toxicity effects on endothelial cells. A Live/Dead assay was used to confirm cell count results. Endothelial cells treated with plasma for short exposure times (5, 15, and 30 s) showed few dead cells (red, FIG. 3C, and quantified in FIG. 3D), confirming that low power plasma treatment is relatively non-toxic at short exposure times. Dead cell number increased with increasing plasma exposure time (p<0.01 by ANOVA). At 60 s, there were nearly two fold the number of dead cells as compared to control. While the dead cell number increased slightly with 60 s plasma treatment, at 120 s of treatment a significant number of dead cells and few live cells (green) were evident. This extensive cytotoxicity may be likely related to sample drying under extended plasma treatment. Therefore, 120 s of plasma exposure was not used for subsequent assays. With the exception of the 120 s plasma treatment time, there was no significant difference between dead cell numbers 3 or 24 hours following plasma exposure. To determine the endothelial cell death mechanism induced by non-thermal plasma treatment, cells were analyzed 24 hours post plasma treatment for apoptosis using the Annexin V-propidium iodide assay. Apoptosis levels increased with plasma treatment time (p<0.01 by ANOVA). At 30 and 60 s plasma treatment, approximately 20% of cells were apoptotic compared to 10% of untreated cells. At the longest treatment time of 120 s, nearly 60% of cells were apoptotic.

Example 10

Endothelial Cell FGF2 Release Following Post Plasma Treatment

Whether FGF2 was released from endothelial cells following non-thermal plasma treatment, and whether the released FGF2 contributed to enhanced cell proliferation was considered. FGF2 has no signal sequence for secretion, and therefore is primarily known to be released during sub-lethal cell membrane damage. The FGF2 level in the media increased up to 3 h after plasma treatment (3.9 J/cm$^2$, 30 s) and then rapidly decreased up to 24 h after plasma treatment (FIGS. 4A and 4B). In contrast, FGF2 media levels for cells treated with 10 ng/ml TNF-α as a positive control rose more slowly but continued to rise up to 24 h.

To understand the role of plasma-induced injury to the cell membrane in FGF2 release, endothelial cell membrane damage was assessed by LDH release 24 h following plasma treatment. Media LDH level increased significantly by 4 h after plasma treatment and continued to rise throughout the first 24 hours (FIG. 4C, p<0.01 by ANOVA), comparable to the TNF-α positive control. The specific role of released FGF2 in enhanced endothelial cell proliferation by plasma treatment was investigated using an FGF2 neutralizing antibody to block FGF2 effects. The FGF2 neutralizing antibody had no significant effect on cells exposed to untreated cell conditioned medium. However, the FGF2 neutralizing antibody significantly suppressed proliferation in endothelial cells exposed to plasma-treated cell conditioned medium (FIG. 4D). The viable cell number for samples incubated in plasma-treated cell conditioned medium with a neutralizing antibody was similar to samples incubated in untreated cell conditioned medium.

What is claimed:

1. A method of inducing endothelial cell proliferation comprising contacting an endothelial cell population with a non-thermal plasma;
   wherein the non-thermal plasma is delivered at an intensity of about 0.5 J/cm$^2$ to about 6 J/cm$^2$; and
   wherein the contacting releases an angiogenic growth factor.

2. The method of claim 1, wherein the angiogenic growth factor is fibroblast growth factor.

3. The method of claim 1, wherein the non-thermal plasma is an atmospheric pressure dielectric barrier discharge.

4. The method of claim 1, wherein the endothelial cell population is directly contacted with the non-thermal plasma.

5. The method of claim 1, wherein the endothelial cell population is indirectly contacted with the non-thermal plasma.

6. The method of claim 1, wherein the endothelial cell population is separately contacted with the non-thermal plasma.

7. The method of claim 1, wherein the endothelial cell proliferation associated with the non-thermal plasma treatment results in a cell population that is at least 50% higher than a control group that has not been subject to the same non-thermal plasma treatment.

8. The method of claim 1, wherein the endothelial cell proliferation associated with the non-thermal plasma treatment results in a cell population that is at least 100% higher than a control group that has not been subject to the same non-thermal plasma treatment.

9. The method of claim 1, wherein the endothelial cell population is contacted with the non-thermal plasma for less than about 30 seconds.

10. The method of claim 1, wherein the endothelial cell population is contacted with the non-thermal plasma for less than about 15 seconds.

11. The method of claim 1, wherein the non-thermal plasma is delivered at an intensity in the range of from about 3 J/cm$^2$ to about 5 J/cm$^2$.

12. The method of claim 1, wherein the endothelial cell population is contacted with a reactive oxygen species produced by the non-thermal plasma.

13. The method of claim 12, wherein the reactive oxygen species are long-living, short-living, or a combination thereof.

14. The method of claim 13, wherein the long-living reactive oxygen species comprise $O_3$, NO, $HO_2$, $H_2O_2$, or any combination thereof.

15. The method of claim 13, wherein the short-living reactive oxygen species comprise OH, O, electrically excited O, $O_2$, or any combination thereof.

16. The method of claim 1, wherein the endothelial cell population is ex vivo tissue.

17. The method of claim 16, wherein the ex vivo tissue is in an organ.

18. The method of claim 1, comprising contacting the endothelial cell population on a patient having a disease, wherein the angiogenic growth factor induces endothelial cell proliferation to promote angiogenesis so as to treat the disease.

19. The method of claim 18, wherein the disease comprises diabetic ulcerative wounds.

20. The method of claim 18, wherein the angiogenic growth factor is fibroblast growth factor-2.

21. The method of claim 18, wherein the non-thermal plasma is an atmospheric pressure dielectric barrier discharge.

22. The method of claim 18, wherein the endothelial cell population is directly contacted with the non-thermal plasma.

23. The method of claim 18, wherein the endothelial cell population is indirectly contacted with the non-thermal plasma.

24. The method of claim 18, wherein the endothelial cell population is separately contacted with the non-thermal plasma.

25. The method of claim 18, wherein the endothelial cell proliferation associated with the non-thermal plasma treatment results in a cell population that is at least 50% higher than a control group that has not been subject to the same non-thermal plasma treatment.

26. The method of claim 18, wherein the endothelial cell proliferation associated with the non-thermal plasma treatment results in a cell population that is at least 100% higher than a control group that has not been subject to the same non-thermal plasma treatment.

27. The method of claim 18, wherein the endothelial cell population is contacted with the non-thermal plasma for about 30 seconds or less.

28. The method of claim 18, wherein the endothelial cell population is contacted with the non-thermal plasma for about 15 seconds or less.

29. The method of claim 18, wherein the non-thermal plasma has an intensity in the range of from about 3 J/cm$^2$ to about 5 J/cm$^2$.

* * * * *